United States Patent [19]

Bollinger et al.

[11] 4,154,958

[45] May 15, 1979

[54] THERMALLY LABILE RUST INHIBITORS

[75] Inventors: Joseph M. Bollinger, North Wales; Richard H. Hanauer, Furlong; Warren H. Machleder, Blue Bell, all of Pa.

[73] Assignee: Rohm and Haas Company, Philadelphia, Pa.

[21] Appl. No.: 737,254

[22] Filed: Oct. 22, 1976

Related U.S. Application Data

[62] Division of Ser. No. 577,269, May 14, 1975, Pat. No. 4,010,007.

[51] Int. Cl.[2] ..................... C07C 69/38; C07C 101/00

[52] U.S. Cl. .................................................... 560/193

[58] Field of Search ............ 260/485 G, 485 L, 485 J; 560/193

[56] References Cited

U.S. PATENT DOCUMENTS

| | | | |
|---|---|---|---|
| 2,292,211 | 8/1942 | Dickey | 260/485 J |
| 3,085,078 | 4/1963 | Fath | 260/485 L |
| 4,020,000 | 4/1977 | Suen et al. | 260/485 G |

*Primary Examiner*—Jane S. Myers

*Attorney, Agent, or Firm*—Lester E. Johnson

[57] ABSTRACT

A new class of thermally labile compounds having rust inhibiting properties is disclosed and claimed. The compounds (or formulations thereof) are especially useful as rust inhibitors when used either alone in distillate hydrocarbon fuels or in multi-purpose additive mixtures for distillate hydrocarbon fuels having a major proportion of hydrocarbon fuel distilling within the gasoline distillation range or other oil compositions to provide rust protection in fuel distribution systems which operate at ambient temperature (e.g., pipelines, tank trucks, and storage tanks). Preferred embodiments of the invention are alkylammonium carboxylate salt-ethoxylated alkyl phenol esters of a dicarboxylic acid.

5 Claims, No Drawings

THERMALLY LABILE RUST INHIBITORS

This is a division of application Ser. No. 577,269 filed May 14, 1975, now U.S. Pat. No. 4,010,007, issued Mar. 1, 1977.

This invention concerns thermally labile compounds such as the alkylammonium carboxylate salt ethoxylated alkyl phenol esters of malonic acid (Formula I) which, when used either alone in distillate hydrocarbon fuels or in multi-purpose additive mixtures for distillate hydrocarbon fuels having a major proportion of hydrocarbon fuel distilling within the gasoline distillation range, are effective as rust inhibitors.

Formula I

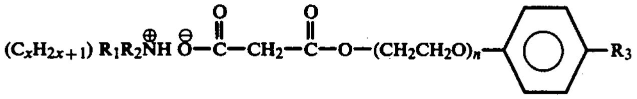

wherein $R_1 = R_2 =$ H or $C_{1-4}$ alkyl, X=4 to 30, $R_3 =$ $C_4H_9$ to $C_{12}H_{25}$ and n = 1 to 12.

It has become apparent that typical rust inhibitors normally do not interfere with carburetor detergency or handling properties. However, their presence, even at very low concentrations, adversely affects induction system detergency. Although the mechanism of interference has not been conclusively established, evidence indicates that because of their surface activity, the rust inhibitors tend to accumulate in the induction system. This has been confirmed by analysis which indicates significant amounts of rust inhibitor in the induction system deposits (ISD). Whatever the mechanism of interference, engine tests clearly demonstrate the adverse effect of rust inhibitors on induction system deposits. Table I shows the effect of 5 ppm of a highly active rust inhibitor (a di-(t-octadecyl-to t-docosylammonium)-carboxylate salt-mono-(triethoxylated octyl phenol) ester of a $C_{54}$ trimer acid which is described herein below as Product 1 on the ISD activity of an excellent commercial additive, Chevron F-310.

TABLE I

| Induction System Deposit Engine Test | | | |
|---|---|---|---|
| Additive | Treating Level, ppm (in gasoline) | Valve & Port Deposits, mg | ASTM D-665 Rust Test-% Area Rusted |
| A | — | 361 | 100 |
| B | 1000 | 11 | 60 |
| C | 1000/5* | 849 | 0 |

*MInimum concentration to obtain 0% rust.

where:

A = Control
B = Chevron F-310
C = Chevron F-310/Product 1

It is evident that in order to formulate a multipurpose additive package with good rust inhibition, a new type of rust inhibitor is needed. Since the rust inhibitor in gasoline is used primarily to provide rust protection in the fuel distribution system which operates at ambient temperatures (pipelines, tank trucks, storage tanks and motor vehicle fuel tanks) and not in the engine induction system which operates at 250°-300° F., compounds that would be readily converted to non-surface active compounds in the engine induction system are indicated. And, since the most effective rust inhibitors that have been developed are invariably salts of carboxylic or phosphoric acid, it was considered that a transition from a salt to a neutral compound would provide a sufficient reduction in surface activity to prevent accumulation of the rust inhibitor in the induction system.

An example of such a transition occurs in the reaction of triethylamine with trimethylborane. At ambient temperature, the product is the salt-like adduct represented by Formula 2. However, at 100° C., the adduct is essentially completely dissociated into neutral components. This reaction is described by the following equation:

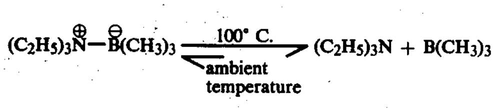

2

The boron-ammonium salts are unfortunately, poor rust inhibitors.

The alkylammonium carboxylate salt — ethoxylated alkyl phenol esters of malonic acid is a system which possesses the structural elements which have been demonstrated to be effective for rust inhibition and which might be expected to undergo a thermal conversion from a surface active compound to neutral, non-surface active components.

The novel salt-ester compounds of this invention which are represented by the general formula Formula I

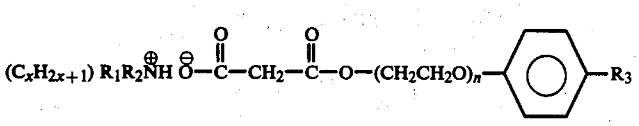

wherein $R_1 = R_2 =$ H or $C_{1-4}$ alkyl; x = 4 to 30; $R_3 =$ $C_4H_9$ to $C_{12}H_{25}$; and n = 1 to 12; are derivatives of the dibasic carboxylic acid, malonic acid, wherein one of the carboxyl groups is esterified by an ethoxylated alkyl phenol functional group possessing 1 to 12 ethoxy groups and an alkyl substituent selected from the group of $C_4H_9$ to $C_{12}H_{25}$, and the second carboxyl group is converted to its alkylammonium salt derivative wherein the alkyl group is selected from a series of $C_4H_9$ to $C_{30}H_{61}$ hydrocarbon functional groups.

The alkylammonium carboxylate salt-ester of malonic acid can be prepared in known fashion by the acid catalyzed esterification of malonic acid with an equimolar amount of a suitable ethoxylated alkyl phenol, followed by a conversion of the remaining carboxyl group to an alkylammonium salt with the addition of a suitable amine. The esterification is ordinarily carried out under reflux conditions in the presence of a suitable aromatic hydrocarbon solvent, e.g, benzene. Typical catalysts are concentrated sulfuric acid and p-toluene-sulfonic acid. The salt formation reaction can be carried out at room temperature or at elevated temperatures, if desired, by treating the ester-acid, either neat or in solution, with the desired amine, followed by customary work-up of the ester-salt product.

The preferred ethoxylated alkyl phenol derivatives employed in this invention are selected from commercially available ethoxylated alkyl phenol compounds which comprise octyl ethoxylated phenol containing 1,3, or 5 equivalents of condensed ethylene oxide and nonyl ethoxylated phenol containing 4 equivalents of condensed ethylene oxide. These commercial compounds are available under the trademarks Triton X-15, Triton X-35, Triton X-45, and Triton N-40, respectively (see Formula 3 below).

Formula 3

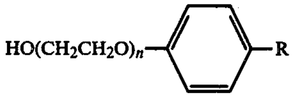

where
Triton X-15 is n = 1, R = $C_8H_{17}$
Triton X-35 is n = 3, R = $C_8H_{17}$
Triton X-45 is n = 5, R = $C_8H_{17}$
Triton N-40 is n = 4, R = $C_9H_{19}$ Preferred embodiments of this invention include commercial tertiary-alkyl primary amine preparations which are available under the trademarks Primene 81-R and Primene JM-T. Primene 81-R is a mixture of t-dodecyl-, t-tridecyl- and t-tetradecyl amines or, principally, a mixture of t-$C_{12}H_{25}NH_2$ to t-$C_{14}H_{29}NH_2$ amines. Primene JM-T is a mixture of t-$C_{18}H_{37}NH_2$ to t-$C_{22}H_{45}NH_2$.

Representative embodiments disclosed and claimed in this invention include the following products:

Product 2 = t-dodecyl- to t-tetradecylammonium salt — pentaethoxylated octyl phenol ester of malonic acid.

Product 3 = t-octadecyl- to t-docosylammonium salt — pentaethoxylated octyl phenol ester of malonic acid.

Product 4 = t-dodecyl- to t-tetradecylammonium salt — tetraethoxylated nonyl phenol ester of malonic acid.

Product 5 = t-octadecyl- to t-docosylammonium salt — tetraethoxylated nonyl phenol ester of malonic acid.

Product 6 = t-dodecyl- to t-tetradecylammonium salt — triethoxylated octyl phenol ester of malonic acid.

Product 7 = t-octadecyl- to t-docosylammonium salt — triethoxylated octyl phenol ester of malonic acid.

Product 8 = t-dodecyl- to t-tetradecylammonium salt — monoethoxylated octyl phenol ester of malonic acid.

Product 9 = t-octadecyl- to t-docosylammonium salt — monoethoxylated octyl phenol ester of malonic acid.

The advantage of rust inhibitors of this type, i.e., thermally labile rust inhibitors, is that, unlike the typical stable rust inhibitors such as the salt-ester derivatives of polycarboxylic acids described in the prior art, the thermally labile compounds decompose to non-surface active components and, thus, do not accumulate in the induction system.

The data presented in Table II demonstrates that the salt-esters of malonic acid when added to gasoline, give good rust inhibition in the ASTM-D-665 Rust Test.

TABLE II

| | Rust Inhibition Test (ASTM D-665) | |
|---|---|---|
| Additive | Treating Level, ppm | % Area Rusted |
| F | — | 100 |
| G | 15 | 3 |
| H | 15 | 5 |
| I | 15,20 | 5, 0 |
| J | 20 | 5 |
| K | 15,20. | 5, 1 |

where:
F = Isooctane control
G = Product 8
H = Product 3
I = Product 7
J = Product 2
K = Product 4

A study of the thermal properties of the salt-ester derivatives of malonic acid provides evidence that these compounds decompose as expected and in the temperature range of 115°-140° C. to give carbon dioxide, the respective amine, and the acetate derivative of the respective ethoxylated phenol derivative. The decomposition of a typical example, Product 2 (the t-dodecyl- to t-tetradecylammonium salt — pentaethoxylated octyl phenol ester of malonic acid), is represented by the following equation:

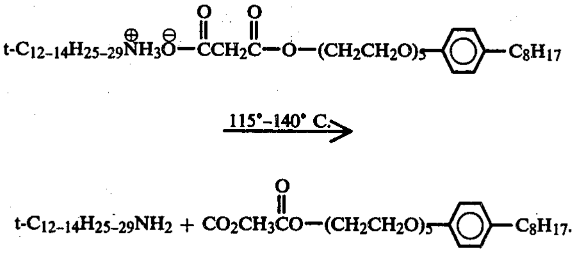

The results presented in Table III indicates a substantial improvement in ISD performance when thermally labile rust inhibitors are substituted for the rust inhibitor Product 1 in gasoline mixtures or gasoline formulations.

TABLE III

Rust and Induction System Performance of Thermally Labile Malonic Salt-Ester Rust Inhibitors

| Additive | Treating Level, ppm | % Area Rusted | Valve & Port Deposits, mg |
|---|---|---|---|
| A | — | 100 | 361 |
| B | 1000 | 60 | 11 |
| C | 1000/5 | 0 | 849 |
| D | 1000/10 | 0 | 373 |

where:
A = Control, gasoline
B = Chevron F-310
C = Chevron F-310/Product 1
D = Chevron F-310/Product 9

The following examples are illustrative of the present invention but are not to be construed as limiting in scope. All percentages throughout the specification and claims are by weight unless otherwise indicated.

EXAMPLE 1

Synthesis of the t-Dodecyl- to t-Tetradecylammonium Salt-Pentaethoxylated Octyl Phenol Ester of Malonic Acid Into a 1-liter reaction flask is charged 78.0g. (0.75 mole) of malonic acid, 319.5g. (0.75 mole) of Triton X-45 (pentaethoxylated octyl phenol, M.W. = 426), 250 ml of benzene and 0.5g of p-toluenesulfonic acid monohydrate. The reaction flask is fitted with a Dean-Stark water collection trap, external heat is added and mechanical stirring is begun. The reaction mixture is heated to reflux and maintained at reflux temperature and stirred for 24 hours, at the end of which period the theoretical amount of water, 13.5g (0.75 mole), is collected. The benzene solvent is removed under reduced pressure (25 mm Hg) and at a temperature of 80° C., using a rotary evaporator and hot water bath. The resulting ester-acid product is allowed to cool to room temperature, and 150g. (0.75 mole) of Primene 81-R (t-alkylamine, $C_{12\text{-}14}H_{25\text{-}29}NH_2$, of M.W. of about 200) is added and thoroughly mixed. The resulting salt-ester product has an acid number of 71.7 (theory 78.4) and % N basic = 1.98 (theory 1.97) and contains about 50 wt. % of the desired product and about 16.5% of di-salt. The amount of di-salt in this product mixture can be reduced to 3–4% by dissolving the half-ester intermediate in a equal volume of hexane and filtering off the precipitated free diacid. The amount of inactive di-Triton X-45 ester can be reduced by charging excess malonic acid initially and then removing it by hexane precipitation and filtration.

EXAMPLE 2

Synthesis of the t-Octadecyl- to t-Docosylammonium Salt—Monoethoxylated Octyl Phenol Ester of Malonic Acid Into a 1-liter reaction flask is charged 78.0g (0.75 mole) of malonic acid, 187.5g. (0.75 mole) of Triton X-15 (monoethoxylated octyl phenol, MW = 250), 250 ml of benzene and 0.5g. of p-toluene-sulfonic acid monohydrate. The reaction flask is fitted with a Dean-Stark water collection trap, external heat is added and mechanical stirring is begun. The reaction mixture is heated to reflux and maintained at reflux temperature and stirred for 24 hours, at the end of which period the theoretical amount of water, 13.5g. (0.75 mole) is collected. The benzene solvent is removed under reduced pressure (25 mm Hg) and at temperature of 80° C., using a rotary evaporator and hot water bath. The resulting ester acid product is allowed to cool to room temperature, and 225g. (0.75 mole) of Primene JM-T (t-alkylamine, $C_{18\text{-}22}H_{37\text{-}45}NH_2$, of M.W. of about 300) is added and thoroughly mixed. The resulting salt-ester product has an acid number of 82.3 (theory 88.1) and % N basic = 2.13 (theory 2.20).

ENGINE TEST EVALUATION OF RUST INHIBITORS

A. Induction System Deposit Engine Test (1) Engine test procedure — The Induction System Deposit Test (ISDT), which is used to evaluate the ability of gasoline additives or mixtures of additives to control induction system deposits (ISD), is run using a new air-cooled, single cylinder, 4 cycle, 2.5 H. P. Briggs and Stratton engine for each test. The engine is run for 150 hours at 3,000 r.p.m. and 4.2 ft. lbs. load, with a one hour shutdown every ten hours to check the oil level. Carbon monoxide exhaust emission measurements are made each hour to insure that a constant air to fuel (A/F) ratio is being maintained.

Upon completion of a test run, the engine is partially disassembled and the intake valve and port are rated and valve and port deposits are collected and weighed. (See Tables I and II).

B. Rust Test Method

The method used for evaluating rust inhibitor additives in industrial hydrocarbon oils and hydrocarbon lubricants is described in ASTM D665, designation 135/64, see pages 235 to 242 of 1972, Annual Book of ASTM Standards, Part 17 (November). Isoctane is used as the control in this test.

In these two test methods, the additive — the alkylammonium carboxylate salt — ethoxylated alkyl phenol esters of malonic acid — is used in minor amounts with a major amount of hydrocarbon fuel. Herein minor amount refers to less than 50% and major amount refers to greater than 50%. In practicing this invention, minor amount refers to less than 1% (10,000 ppm) but greater than 0%, preferably 5 ppm to 1,000 ppm and major amount refers to greater than 99% but less than 100%.

We claim:

1. A thermally labile alkylammonium carboxylate salt-ethoxylated alkyl phenol ester of malonic acid represented by the formula:

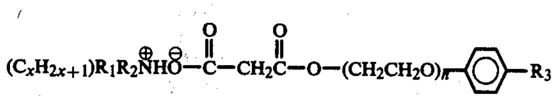

wherein the group $C_xH_{2x+1}$ is a t-alkyl group wherein x = 12 to 22, n = 1 to 5, $R_1 = R_2 = H$ and $R_3 = C_8H_{17}$ or $C_9H_{19}$.

2. A composition according to claim 1 wherein x = 12 to 14, n = 5 and $R_3 = C_8H_{17}$.

3. A composition according to claim 1 wherein x = 18 to 22, n = 5 and $R_3 = C_8H_{17}$.

4. A composition according to claim 1 wherein x = 18 to 22, n = 3 and $R_3 = C_8H_{17}$.

5. A composition according to claim 1 wherein x = 18 to 22, n = 1 and $R_3 = C_8H_{17}$.

* * * * *